United States Patent
Smith et al.

(10) Patent No.: US 10,046,252 B2
(45) Date of Patent: Aug. 14, 2018

(54) SAND SEPARATOR INTERFACE DETECTION

(71) Applicant: Micro Motion, Inc., Boulder, CO (US)

(72) Inventors: Stephen Dewhurst Smith, Middlesex (GB); Simon P. H. Wheeler, Erie, CO (US)

(73) Assignee: Micro Motion, Inc., Boulder, CO (US)

( * ) Notice: Subject to any disclaimer, the term of this patent is extended or adjusted under 35 U.S.C. 154(b) by 253 days.

(21) Appl. No.: 14/782,908

(22) PCT Filed: Apr. 15, 2014

(86) PCT No.: PCT/US2014/034164
§ 371 (c)(1),
(2) Date: Oct. 7, 2015

(87) PCT Pub. No.: WO2014/179050
PCT Pub. Date: Nov. 6, 2014

(65) Prior Publication Data
US 2016/0059153 A1    Mar. 3, 2016

Related U.S. Application Data

(60) Provisional application No. 61/817,104, filed on Apr. 29, 2013.

(51) Int. Cl.
*B01D 21/30* (2006.01)
*G01F 23/296* (2006.01)
(Continued)

(52) U.S. Cl.
CPC .......... *B01D 21/302* (2013.01); *B01D 21/245* (2013.01); *B01D 21/2483* (2013.01);
(Continued)

(58) Field of Classification Search
CPC  B01D 21/245; B01D 21/2483; B01D 21/267; B01D 21/302; B01D 21/34; G01F 23/296; G01F 23/2967; G01F 2009/006
See application file for complete search history.

(56) References Cited

U.S. PATENT DOCUMENTS 4,226,714 A    10/1980  Furness et al.
5,879,541 A    3/1999   Parkinson
(Continued)

FOREIGN PATENT DOCUMENTS

CN    101506625 A    8/2009
CN    101517382 A    8/2009
(Continued)

OTHER PUBLICATIONS

Vega Level and Pressure Operating Instruction Manual (Year: 1996).*

*Primary Examiner* — Terry K Cecil
(74) *Attorney, Agent, or Firm* — The Ollila Law Group LLC (57) ABSTRACT

A sand separator is provided that includes a separation chamber and a drain. The sand separator comprises a meter in fluid communication with an interior of the separation chamber, wherein the meter is configured to detect a liquid/solid interface. Meter electronics in electrical communication with the meter are configured to receive a signal from the meter indicating the liquid/solid interface.

20 Claims, 5 Drawing Sheets

(51) Int. Cl.
  *B01D 21/24* (2006.01)
  *B01D 21/26* (2006.01)
  *B01D 21/34* (2006.01)
  *G01N 9/00* (2006.01)

(52) U.S. Cl.
  CPC ........... *B01D 21/267* (2013.01); *B01D 21/34* (2013.01); *G01F 23/296* (2013.01); *G01F 23/2967* (2013.01); *G01N 2009/006* (2013.01)

(56) References Cited

U.S. PATENT DOCUMENTS

| | | |
|---|---|---|
| 5,895,848 A | 4/1999 | Wilson et al. |
| 6,138,507 A | 10/2000 | Getman et al. |
| 6,444,119 B1 * | 9/2002 | Mains, Jr. .......... B01D 17/0205 210/130 |
| 2010/0043554 A1 | 2/2010 | D'Angelico et al. |
| 2010/0083752 A1 | 4/2010 | Malinek |
| 2012/0174671 A1 | 7/2012 | Urban |

FOREIGN PATENT DOCUMENTS

| | | |
|---|---|---|
| CN | 102549399 A | 7/2012 |
| JP | 4-4096 A | 1/1992 |
| JP | 2003-194614 A | 7/2003 |
| WO | 1996004058 A1 | 2/1996 |
| WO | 0116591 A1 | 3/2001 |

* cited by examiner

SAND SEPARATOR INTERFACE DETECTION

FIELD OF THE INVENTION

The embodiments described below relate to sand separators, and more particularly, to improved sand separators for detection of a liquid/solid interface therein.

BACKGROUND

Separator technology is commonly used in wells worldwide, be it a test separator or a production separator. The separators used in sand control completions, for example, are particularly prone to filling with sand. This issue is particularly problematic in relation to off-shore installations where the shut-down of production to clear out a separator can cause significantly delayed production and related financial losses.

Sand separators are also often to protect test or production equipment when large amounts of sand are anticipated as part of the process at hand (hydraulic fracturing, sand control applications, or oil sand applications for example). Prior warning of sand accumulation in a separator is key to minimizing downtime and delayed production, which is typically accomplished via planning and scheduling of routine separator maintenance.

As an example, exploration for methane, or natural gas, involves injection of high-pressure fluids (mostly water with sand) directly into underground rock formations expected to yield natural gas. In hydraulic fracturing procedures, water pressure fractures the rock strata, whereupon entrapped natural gas escapes into a well bore and is captured at the surface. Hydraulic fracturing fluid is recovered from the exploration wells and disposed of, usually by hauling it off in trucks to a remote disposal site. This fluid contains a considerable amount of fracturing sand. The sand is used to help hold open cracks to maximize escape of natural gas from within the strata. Fracturing sand is also used to clean and etch formations so to promote maximum gas delivery. The sand present in fracturing fluid doesn't all remain lodged in the formation, so some returns to the surface in what is called the "flowback" from the well. The flowback fluid includes a significant quantity of injected fracturing sand, as well as silt and rock debris flushed from the rock strata. Such sand and debris can clog or damage pipes, valves, pumps, and other portions of the system. Sand separators prevent these particulates from clogging and damaging the system, but only to the extent that the sand separator is functional. This is merely provided as an example to illustrate one use for sand separators.

In general, a sand separator is used to separate sand or other solids from a liquid/solid mix, and for continued operation of sand separators, a reliable indication of the level of sand in the separator is required. If the sand level is not correctly calculated, there is a risk the sand separator will over-fill. Once over-filled, the typical remedy is to halt the process at hand and manually empty the sand and debris from the separator. Of course, during such corrective actions neither the sand separator nor the production equipment attached thereto is usable, thus facilities incur production down-time and related financial losses.

There is a need for means to eliminate or reduce sand separator clogging. The embodiments described below overcome these and other problems and an advance in the art is achieved. The embodiments described below provide a sand separator that detects the sand level in the collection chamber having a vibratory meter.

Vibratory meters, such as vibratory densitometers and vibratory viscometers, typically operate by detecting motion of a vibrating element that vibrates in the presence of a fluid material to be measured. Properties associated with the fluid material, such as density, viscosity, temperature, and the like, can be determined by processing measurement signals received from motion transducers associated with the vibrating element. The vibration modes of the vibrating element system generally are affected by the combined mass, stiffness, and damping characteristics of the vibrating element and the surrounding fluid material.

One example of a vibratory density or viscosity meter operates on the vibrating element principle, wherein the element is a slender tuning fork structure which is immersed in the liquid being measured. A conventional tuning fork consists of two tines, typically of flat or circular cross section, that are attached to a cross beam, which is further attached to a mounting structure. The tuning fork is excited into oscillation by a driver, such as a piezo-electric crystal for example, which is internally secured at the root of the first tine. The frequency of oscillation is detected by a second piezo-electric crystal secured at the root of the second tine. The transducer sensor may be driven at its first natural resonant frequency, as modified by the surrounding fluid, by an amplifier circuit located with the meter electronics.

When the fork is immersed in a fluid and excited at its resonant frequency, the fork will move fluid via the motion of its tines. The resonant frequency of the vibration is strongly affected by the density of the fluid these surfaces push against whilst the fluid viscosity has a significant effect on the bandwidth. As the viscosity of the fluid changes, the overall damping forces change, changing the bandwidth and with it the "Q" or quality factor of the sensor. An electronic circuit may excite the sensor into oscillation alternately at two positions on a frequency response curve, and in doing this, the quality factor (Q) of the resonator may be determined as well as the resonant frequency. By measuring certain periods related to the frequency response curve, the viscosity of a fluid can be calculated.

In particular, the viscosity of a fluid can be measured by generating vibration responses at frequencies $\omega_1$ and $\omega_2$ that are above and below a resonant frequency $\omega_0$ of the combined fluid and vibratory sensor. At the resonance frequency $\omega_0$, the phase difference $\Phi_0$ may be about 90 degrees. The two frequency points $\omega_1$ and $\omega_2$ are defined as the drive frequencies where the drive signal phase and the vibration signal phase differ by the phase differences $\Phi_1$ and $\Phi_2$, respectively. The phase difference $\Phi_1$ may be defined as the point where the phase difference between the drive signal phase and the vibration signal phase is about 135 degrees, for example. The phase difference $\Phi_2$ may be defined as the point where the phase difference between the drive signal phase and the vibration signal phase is about 45 degrees, for example.

The distance between these two frequency points $\omega_1$ and $\omega_2$ (i.e., the difference in frequency between $\omega_1$ and $\omega_2$) is used to determine the term Q, which is proportional to viscosity and can be approximated by the formula:

$$\text{viscosity} \approx Q = \omega_0/(\omega_1 - \omega_2)$$

The resonant frequency ω0 is centered between the two frequency points ω1 and ω2. Therefore, the resonant frequency ω0 can be defined as:

$$\omega 0 \approx 0.5*(\omega 1 + \omega 2)$$

The frequency points, ω1 and ω2, are determined during operation when the sensor element interacts with the fluid to be characterized. In order to properly determine the frequency points ω1 and ω2, the drive system uses a closed loop drive, driving the sensor element to alternate between the two phase difference points Φ1 and Φ2) and recording the vibration frequencies ω1 and ω2 at these points. By using a closed-loop drive, the prior art drive system ensures that the phase difference measurement is stable when the vibration frequencies ω1 and ω2 are determined. This serves as an example of how phase may be used to calculate viscosity by meter electronics.

By orienting a vibratory meter in a sand collection reservoir of a sand separator, and measuring changes in pickoff sensor signal strength and/or signal phase differences, the liquid/solid interface level in a sand separator is rendered detectable, as is disclosed herein.

SUMMARY OF THE INVENTION

A sand separator including a separation chamber and a drain is provided according to an embodiment. According to an embodiment, the sand separator comprises a meter in fluid communication with an interior of the separation chamber, wherein the meter is configured to detect a liquid/solid interface. The sand separator further comprises meter electronics in electrical communication with the meter configured to receive a signal from the meter.

A sand separator including a separation chamber and a drain is provided according to an embodiment. According to an embodiment, the sand separator comprises a vibratory fork densitometer in fluid communication with an interior of the separation chamber that is configured to indicate a liquid/solid interface. The sand separator also comprises a vibratory element of the fork densitometer that is configured to vibrate. Additionally, the sand separator comprises a driver configured to receive a driver signal, wherein the driver is further configured to vibrate the vibratory element, and also a pickoff sensor configured to detect a vibration of the vibratory element and generate a pickoff signal that represents the vibration detected. The sand separator further comprises meter electronics in electrical communication with the fork densitometer is configured to provide the driver signal to the driver and receive the pickoff signal from the fork densitometer.

A method of detecting a liquid/solid interface in a sand separator is provided according to an embodiment. According to an embodiment, the method comprises the steps of: vibrating a vibratory element located in a sand separator; measuring a vibrational response of the vibratory element; comparing the vibrational response to a reference value; and detecting a level of the liquid/solid interface in the sand separator.

A method of detecting a liquid/solid interface in a sand separator is provided according to an embodiment. According to an embodiment, the method comprises the steps of: placing a vibratory meter in a sand separator; vibrating a vibratory element of the vibratory meter at a resonant frequency of the vibratory element and fluid surrounding the vibratory element; receiving a signal from a pickoff sensor of the vibratory meter; and detecting a presence of the liquid/solid interface.

ASPECTS

According to an aspect, a sand separator including a separation chamber and a drain, comprises: a meter in fluid communication with an interior of the separation chamber, wherein the meter is configured to detect a liquid/solid interface; and meter electronics in electrical communication with the meter configured to receive a signal from the meter.

Preferably, the meter is located proximate a level in the separation chamber that corresponds to a maximum desired level of the liquid/solid interface.

Preferably, the meter is a vibratory meter.

Preferably, the vibratory meter is a densitometer.

Preferably, the sand separator further comprises: a vibratory element; a driver configured to vibrate the vibratory element; and a pickoff sensor configured to detect vibration of the vibratory element.

Preferably, the signal from the sensor is a signal strength of the pickoff sensor.

Preferably, the signal strength is a voltage.

Preferably, the signal from the meter is a phase difference between a driver signal provided to the driver and a pickoff signal received from the pickoff sensor.

Preferably, the drain is remotely actuatable.

Preferably, the driver comprises a piezoelectric element, and the pickoff sensor comprises a piezoelectric element.

According to an aspect, a sand separator including a separation chamber and a drain, comprising:

a vibratory fork densitometer in fluid communication with an interior of the separation chamber that is configured to indicate a liquid/solid interface;

a vibratory element of the fork densitometer that is configured to vibrate;

a driver configured to receive a driver signal, wherein the driver is further configured to vibrate the vibratory element;

a pickoff sensor configured to detect a vibration of the vibratory element and generate a pickoff signal that represents the vibration detected; and meter electronics in electrical communication with the fork densitometer configured to provide the driver signal to the driver and receive the pickoff signal from the fork densitometer.

Preferably, the pickoff signal is a signal strength of the pickoff sensor.

Preferably, the pickoff signal strength is a voltage.

Preferably, the meter electronics calculate a phase difference between the driver signal and the pickoff signal.

Preferably, the sand separator further comprises a drain configured to release material from the sand separator.

Preferably, the drain comprises a valve that is actuatable by the meter electronics.

According to an aspect, a method of detecting a liquid/solid interface in a sand separator comprising the steps of:

vibrating a vibratory element located in a sand separator;

measuring a vibrational response of the vibratory element;

comparing the vibrational response to a reference value; and detecting a level of the liquid/solid interface in the sand separator.

Preferably, the method further comprises the step of indicating the presence of the liquid/solid interface in the sand separator if an intensity of the vibrational response is below a predetermined threshold.

Preferably, the method further comprises the step of indicating the presence of the liquid/solid interface in the sand separator if a phase difference between the vibrational response and the reference value is below a predetermined threshold.

Preferably, the method further comprises the step of emptying solids from the sand separator if the liquid/solid interface exceeds a predetermined level.

Preferably, the method further comprises the step of opening a drain of the sand separator.

According to an aspect, a method of detecting a liquid/solid interface in a sand separator comprising the steps of:
placing a vibratory meter in a sand separator;
vibrating a vibratory element of the vibratory meter at a resonant frequency of the vibratory element and fluid surrounding the vibratory element;
receiving a signal from a pickoff sensor of the vibratory meter; and
detecting a presence of the liquid/solid interface.

Preferably, the method further comprises the step of maintaining a fixed phase difference between a drive signal and a pickoff signal.

Preferably, the fixed phase difference is approximately 45°.

Preferably, the method further comprises the step of indicating when the vibratory meter is unable to maintain the fixed phase difference between the drive signal and the pickoff signal.

Preferably, the method further comprises the step of indicating when the phase difference between the drive signal and the pickoff signal fluctuates from the fixed phase difference by greater than a predetermined amount.

Preferably, the method further comprises the step of indicating when the vibratory element ceases to vibrate.

Preferably, the method further comprises the step of indicating the presence of the liquid/solid interface in the sand separator if an intensity of the vibrational response is below a predetermined threshold.

Preferably, the intensity comprises a voltage.

Preferably, the method further comprises the step of emptying solids from the sand separator if the liquid/solid interface is detected.

Preferably, the method further comprises the step of opening a drain of the sand separator.

BRIEF DESCRIPTION OF THE DRAWINGS

The same reference number represents the same element on all drawings. The drawings are not necessarily to scale.

DETAILED DESCRIPTION OF THE INVENTION

FIGS. 1-5 and the following description depict specific examples to teach those skilled in the art how to make and use the best mode of embodiments of a sand separator and related methods. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
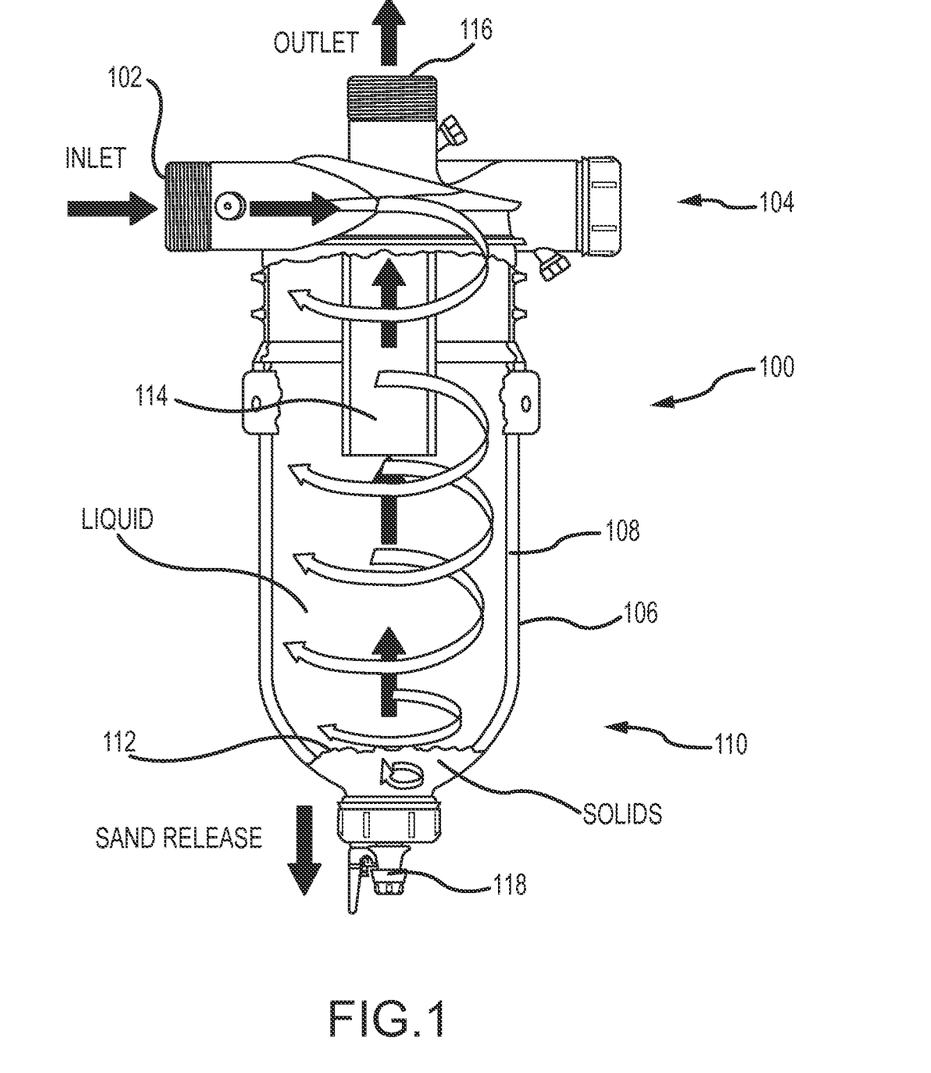
FIG. 1 illustrates a prior art sand separator.

FIG. 1 illustrates a prior art sand separator 100. An inlet port 102 allows a liquid/solid mixture to enter the sand separator 100 for the purpose of separating the liquid phase from the solid phase of the mixture. Typically, sand, sediment, and debris (collectively "solids") that is carried in water is separated from the water. However, other liquids and solids are contemplated by the present embodiments, and no example provided herein should be considered as limiting the scope of the fluid that can comprise a liquid. The fluid can comprise a gas. Alternatively, the fluid can comprise a multi-phase fluid, such as a liquid that includes entrained gas, entrained solids, multiple liquids, or combinations thereof.

The inlet port 102 is positioned proximate a top region 104 of the separator 100 and is offset from a vertical axis such that the mixture enters the separator 100 somewhat tangentially so that a circular flow pattern is created inside the separation chamber 106. This flow pattern, through centrifugal forces, causes heavier solids to travel to an inner surface 108 of the separation chamber 106. The solids tend to drop towards a bottom region 110 of the separator 100 and eventually fall into a solids retention region 112. The solids retention region 112 is merely a portion of the bottom region 110 of the separator 100 in this embodiment. In other embodiments, separate chambers for sand collection are contemplated. Liquid that is substantially free of solids is drawn through a conduit 114 and exits the separator 100 through an outlet port 116. In order to purge accumulated solids, a drain 118 is situated proximate the solids chamber 112 that can be opened to release these solids. The drain may comprise a valve. As will be apparent to one skilled in the art, if the solids accumulate past a particular level in a particular separator 100, the separator 100 may clog, and solids will need to be manually purged in a fashion not in line with flow processes, thereby disrupting such processes.

Figure 2:
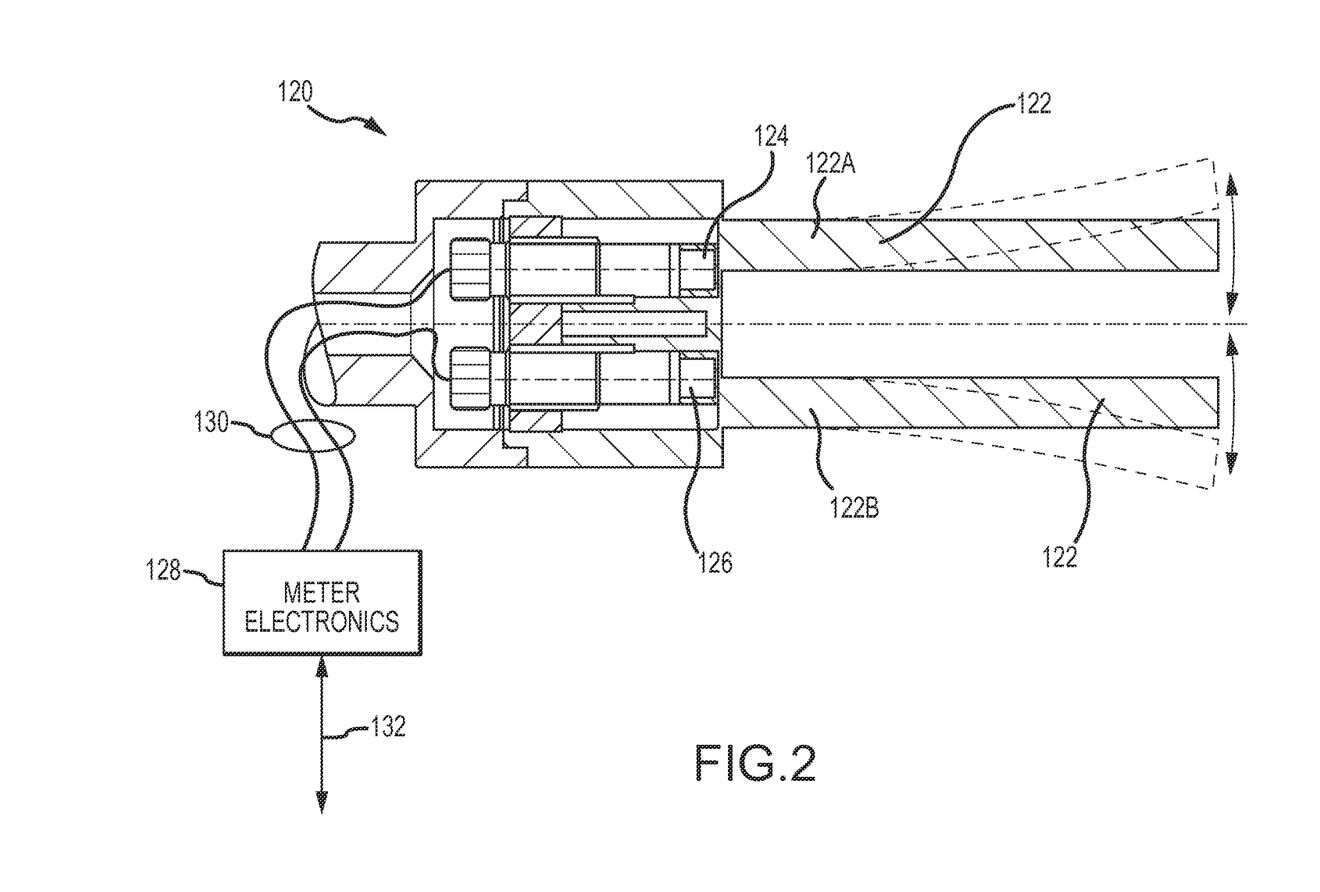
FIG. 2 illustrates an embodiment of a vibratory densitometer.

To detect the liquid/solid interface in a sand separator 100, an embodiment provided utilizes a vibratory meter 120. FIG. 2 illustrates a vibratory meter 120. A vibratory element 122 (typically having a "fork" or "tine" design) is driven to vibrate at a frequency by a driver 124. A pickoff sensor 126 with the vibratory element 122 detects vibration of the vibratory element 122. Meter electronics 128 are connected to the driver 124 and pickoff sensor 126. Vibratory meters without forks or tines are also contemplated.

The meter electronics 128 may provide electrical power to the vibratory element 122 via the lead or leads 130. The leads 130 comprise connections for data, power, and the like from a power supply (not shown), meter electronics 128, or other control or computing devices (not shown). The meter electronics 128 may control operation of the meter 120 and vibratory element 122 via the lead or leads 100. For example, the meter electronics 128 may generate a drive signal and supply the drive signal to the driver 124, wherein the vibratory element 122 is driven to generate a vibration in one or more vibratory components, such as individual tines, using the drive signal. The drive signal may control the vibrational amplitude and/or may control the vibrational frequency. The drive signal may also control the vibrational duration and/or vibrational timing or phase.

The meter electronics 128 receives a vibration signal or signals from the vibratory element 122 via the lead or leads 130. The meter electronics 128 may process the vibration signal or signals in order to generate a density or viscosity measurement, for example. It should be understood that other or additional measurements may be generated from the vibration signal or signals. In one embodiment, the meter electronics 128 process the vibration signal or signals received from the vibratory element 122 to determine a frequency of the signal or signals. The frequency may comprise a resonant frequency of the vibratory element/fluid, which may be used to determine a density or viscosity of the fluid. In related embodiments, signals from the meter electronics 128 are sent to other computing or process devices for processing.

The meter electronics 128 may also process the vibration signal or signals to determine other characteristics of the fluid, such as a viscosity or a phase shift between signals that can be processed to determine a fluid flow rate, for example. Other vibrational response characteristics and/or fluid measurements are contemplated and are within the scope of the description and claims, such as the presence of solids suspended in a liquid and the presences of a liquid/solid interface. The meter electronics 128 may be further coupled to an interface 132, and the meter electronics 128 may communicate signals via this interface 132. The meter electronics 128 may process the received vibration signal to generate a measurement value or values and may communicate a measurement value or values via the interface 132. In addition, the meter electronics 128 may receive information over the interface 132, such as commands, updates, operational values or operational value changes, and/or programming updates or changes. In addition, the interface 132 can enable communications between the meter electronics 128 and a remote processing system (not shown). The interface 132 is capable of any manner of electronic, optical, or wireless communication, such as for example 4-20 ma, HART, RS-485, Modbus, Fieldbus, and the like, without limitation.

In an embodiment, the driver 124 and pickoff sensor 126 each comprise piezo-electric crystal elements. The driver 124 and pickoff sensor 126 are located adjacent to first 122A and second tines 122B of the vibratory element 122. The driver 124 and pickoff sensor 126 are configured to contact and mechanically interact with the first and second tines 122A, 122B. In particular, the driver 124 may contact at least a portion of the first tine 122A. The driver 124 expands and contracts when subjected to a drive signal or reference signal provided by meter electronics 128. As a result, the driver 124 alternatingly deforms and therefore displaces the first tine 122A from side to side in a vibratory motion (see dashed lines), disturbing the fluid in a periodic, reciprocating manner. Vibration of the second tine causes a corresponding electrical signal to be generated by the pickoff sensor 124. The pickoff sensor 124 transmits the vibration signal to the meter electronics 128. The meter electronics 128 processes the vibration signal and may measure the vibration signal amplitude and/or the vibration signal frequency of the vibration signal. The meter electronics 128 may also compare the phase of the signal from the pickoff sensor 124 to a reference phase signal that is provided by the meter electronics 128 to the driver 124. Meter electronics 128 may also transmit the vibration signal via the interface 132.

The vibratory meter 120 is at least partially immersed into a fluid to be characterized. For example, the vibratory meter 120 may be mounted in a pipe or conduit. The vibratory meter 120 may be mounted in a tank or container or structure for holding a fluid. The vibratory meter 120 may be mounted in a manifold or similar structure for directing a fluid flow. In a preferred embodiment, the vibratory sensory is mounted such that the vibratory element 122 projects into an interior of a separation chamber 106 of a sand separator 100. Other mounting arrangements are contemplated, however, and are within the scope of the description and claims.

Figure 3:
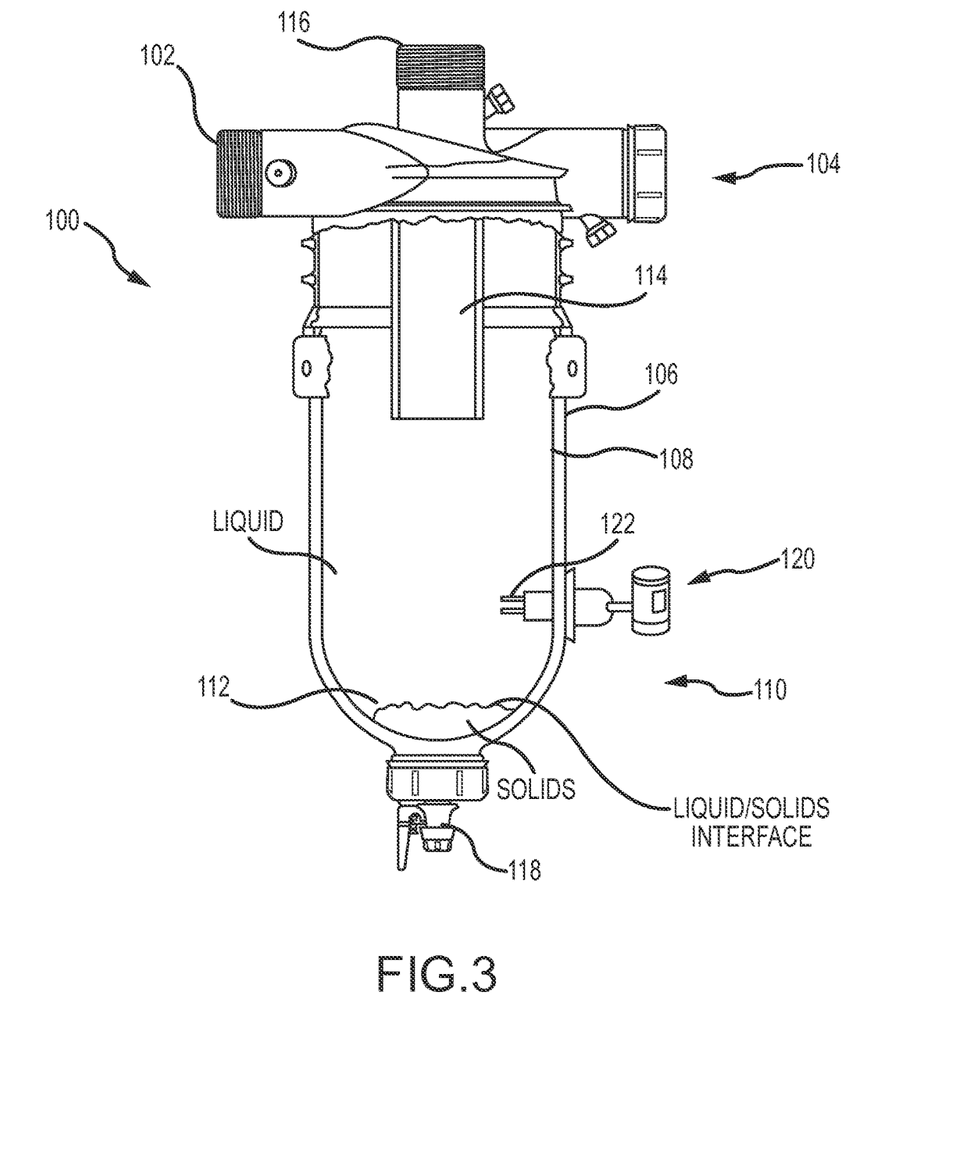
FIG. 3 illustrates an embodiment of sand separator with a liquid/solid interface detector.

FIG. 3 illustrates an embodiment of a sand separator 100 with a meter 120 for indicating a liquid/solid interface level. A meter 120 is placed on the separation chamber 106 such that the portion thereof required to sense the solid/liquid interface is disposed inside the separation chamber 106. In an embodiment, the meter 120 is a vibratory meter. In a related embodiment, the meter 120 is a vibratory fork densitometer. In this case, a vibratory element 122 projects into the separation chamber 106 so that tines 122A, 122B of the vibratory element 122 are capable of fluid contact.

Liquid enters the inlet port 102 of the separator 100 in a tangential orientation so that a circular flow pattern is created inside the separation chamber 106. This flow pattern, through centrifugal forces, forces solids against the inner surface 108 of the separation chamber 106 where the solids tend to drop towards a bottom region 110 of the separator 100 and eventually fall into a solids retention region 112. A drain 118 on the bottom of the separation chamber 106 may be opened so that solids are purged from the separator 100. If the level of solids rises too far, the separator 100 will clog and be rendered inoperable. In an embodiment, the meter 120 is positioned at a position on the separation chamber 106 that corresponds to the maximum desired level of the liquid/solid interface. When the liquid/solid interface rises to this level, the meter 120 detects the interface.

In an embodiment, the drain 118 is remotely actuatable, so that a signal, such as an electric, electronic, pneumatic, hydraulic, or similar signal causes the drain 118 to open. In an embodiment, when the liquid/solid interface reaches a predetermined maximum desired level, the meter 120 detects this interface through meter electronics 128 and communicates with the drain 118 such that the drain 118 actuates so that at least a portion of the solids content within the separator 100 is purged from therein. In particular, meter electronics 128 receive a signal from the meter 120 that indicates the presence of the liquid/solid interface, and this is processed by the meter electronics 128 which sends a signal to the drain 118 to open and purge the separator.

In an embodiment, the meter 120 is a densitometer, and in a related embodiment, the meter is a vibratory fork densitometer. The densitometer has a vibratory element 122 that projects into the separation chamber 106, wherein the vibratory element 122 is driven to vibrate by a driver 124 and a pickoff sensor 126 detects vibrations. In the case of a vibratory fork densitometer, a first tine 122A is driven to vibrate by a driver 124 and a second tine 122B transmits vibrations to a pickoff sensor 126. In either case, the meter electronics 128 provides a drive or reference signal to the driver 124 and receives a signal from the pickoff sensor 126 that represents the vibration detected thereby. It is the signal from the pickoff sensor 126 that is analyzed by the meter electronics (or relayed to an interface 132) that may be particularly indicative of a liquid/solid interface.

In an embodiment, the meter electronics 128 receives a signal from the pickoff sensor 126 that indicates the strength of the signal. In an embodiment, the signal strength is measured by a voltage. When the vibratory element 122 is immersed in a predominantly liquid phase, the tines 122A, 122B vibrate, and the pickoff sensor 126 outputs a voltage of between about 4 mV and 20 mV, for example without limitation. Other voltages and voltage ranges are contemplated, and nothing herein shall be construed as limiting the voltages to those exemplified. As the liquid/solid interface rises due to solids accumulating in the sand separator 100, the first tine 122A and second tine 122B will increasingly vibrate at a lower intensity, thus the pickoff sensor 126 outputs a lower voltage, such as a voltage that is less than 4 mV, for example. As the tines 122A, 122B are covered by more and more solids, the output will lower and approach, if not reach, 0 mV. As this happens, besides a lowering of the output voltage, an instability in voltage readings is also detectable. The output may also comprise a digital signal. The output may be modified, such as for example, with a calibration coefficient. Meter electronics 128 detect the lowered voltage and/or increased instability and signal the sand separator 100 to open the drain 118. The threshold voltage for initiating the opening of the drain 118 is saved in meter electronics 128, and may be predetermined and set by the factory during production and/or may be user-adjustable. Once the solids are purged, the meter 120 outputs a voltage that indicates the presence of a predominantly liquid phase, and controls the drain 118 to close. The amount of time the valve 118 remains open may be preset, or based on meter 120 parameters, or both. In embodiments without automated drain actuation, the meter 120 or meter electronics 128 alerts a user that the drain 118 should be opened or closed.

In another embodiment, a phase difference is utilized to detect the liquid/solid interface. In particular, the meter electronics 128 signal the driver 124 to cause the vibratory element 122 to vibrate. The vibration is at a resonant frequency of the vibratory element in the surrounding medium. If the density or viscosity of the medium changes, so does the resonant frequency and bandwidth. Therefore, the resonant frequency of the vibratory element 122 will change as the liquid/solid interface approaches due the percentage of solids in the medium increases with interface level. As the solids cover the vibratory element 122, the vibratory response is altered, and the vibratory element 122 may eventually cease to vibrate altogether as it is buried.

Meter electronics 128 signal the driver 124 to cause the vibratory element 122 to vibrate at a particular frequency. The meter electronics 128 then detect the signal from the pickoff sensor 126, and maintain a fixed phase difference between the signal from the pickoff sensor 126 and the reference signal sent to the driver 124 in a closed-loop fashion. In a preferred embodiment, the fixed phase difference is about 45°. Other degrees of phase difference are contemplated, however. While maintaining the phase difference, at least one drive frequency ($\omega$) is measured, and the meter electronics 128 may calculate a fluid density and other fluid properties. As the liquid/solid interface rises to contact the vibratory element, the driver 124 is unable to be driven at a frequency that maintains a fixed phase difference between the driver signal and pickoff sensor signal, which is due to the solids interfering with the vibratory element 122. This results in the phase difference between the driver signal and pickoff sensor signal becoming unstable at first and to eventually fluctuate away from the fixed point. As the phase difference drifts, meter electronics construe this as the presence of the liquid/solid interface. In an embodiment, when meter electronics 128 detect this phase drift, the sand separator 100 is signaled to open the drain 118. The threshold phase difference for initiating the opening of the drain 118 is saved in meter electronics 128, and may be predetermined and set by the factory during production and/or may be user-adjustable. Once the solids are substantially purged, the meter 120 outputs a restored fixed phase difference that indicates the presence of a predominantly liquid phase, and the drain 118 is signaled to close. The amount of time the valve 118 remains open may be preset, or based on meter 120 parameters, or both. In embodiments without automated drain actuation, the meter 120 alerts a user that the drain 118 should be opened or closed.

Figure 4:
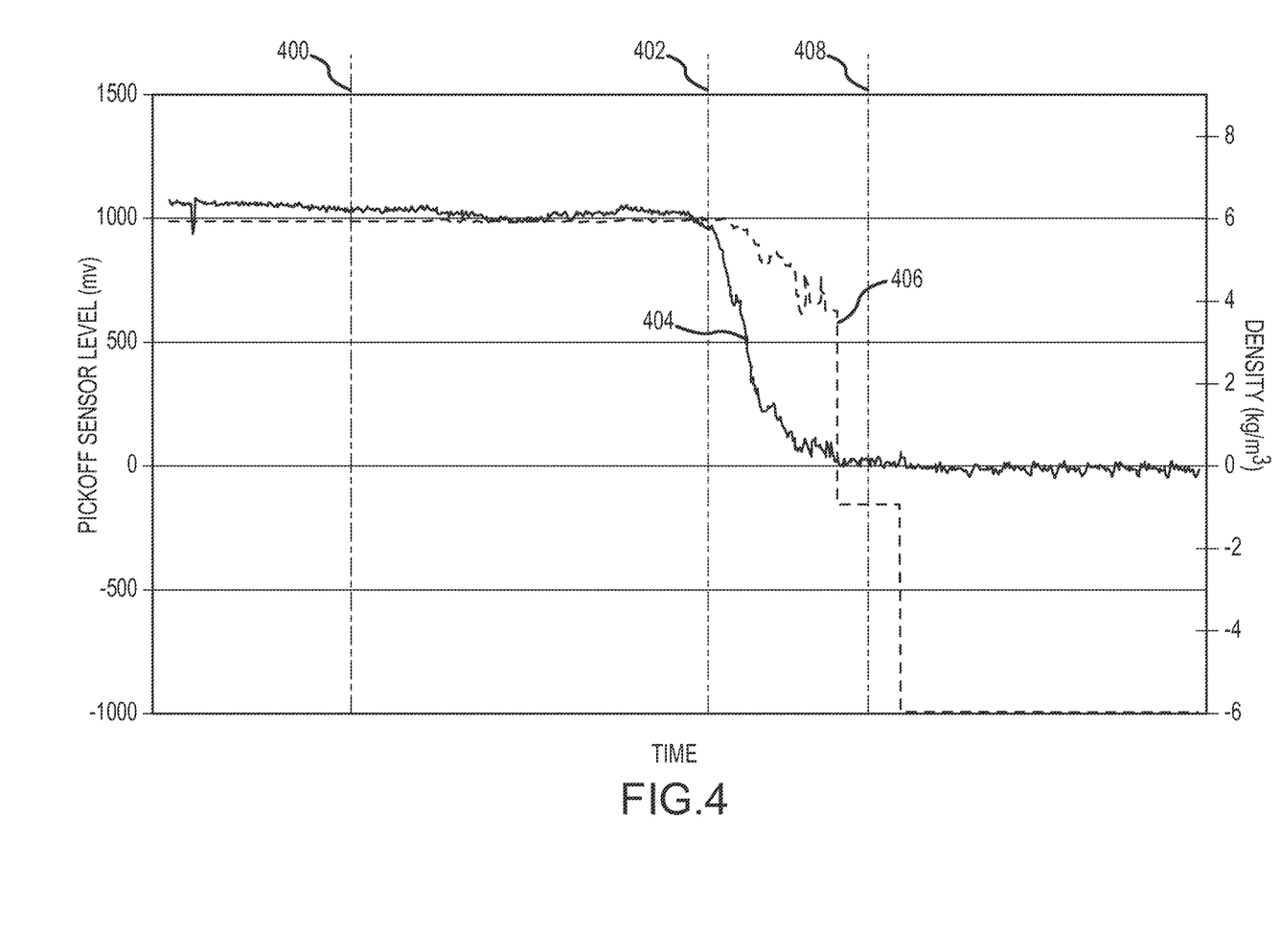
FIG. 4 is a graph illustrating a sand separator with a liquid/solid interface detector in use.

FIG. 4 shows data for a vibratory meter 120 installed in a sand separator 100 wherein sharp sand is introduced into the separator 100. The sharp sand is introduced into the separator 100 at a first point 400. At a second time point 402, the liquid/solid interface is initially detected by the meter 120. The vibratory element 122 at this point is interacting with an increasingly greater proportion of sand as the liquid/solid interface rises. The pickoff sensor output 404 reflects this by exhibiting a decreasing output voltage. The meter output 406 (measured as density in this example) concurrently decreases as a function of the pickoff sensor output 404. At a third time point 408, the vibratory element 122 is substantially buried by the sharp sand, and the vibratory element 122 is dampened to a point that the pickoff sensor output 404 is effectively about 0 mv. This, of course, is reflected by the meter output 406, which also declines.

Figure 5:
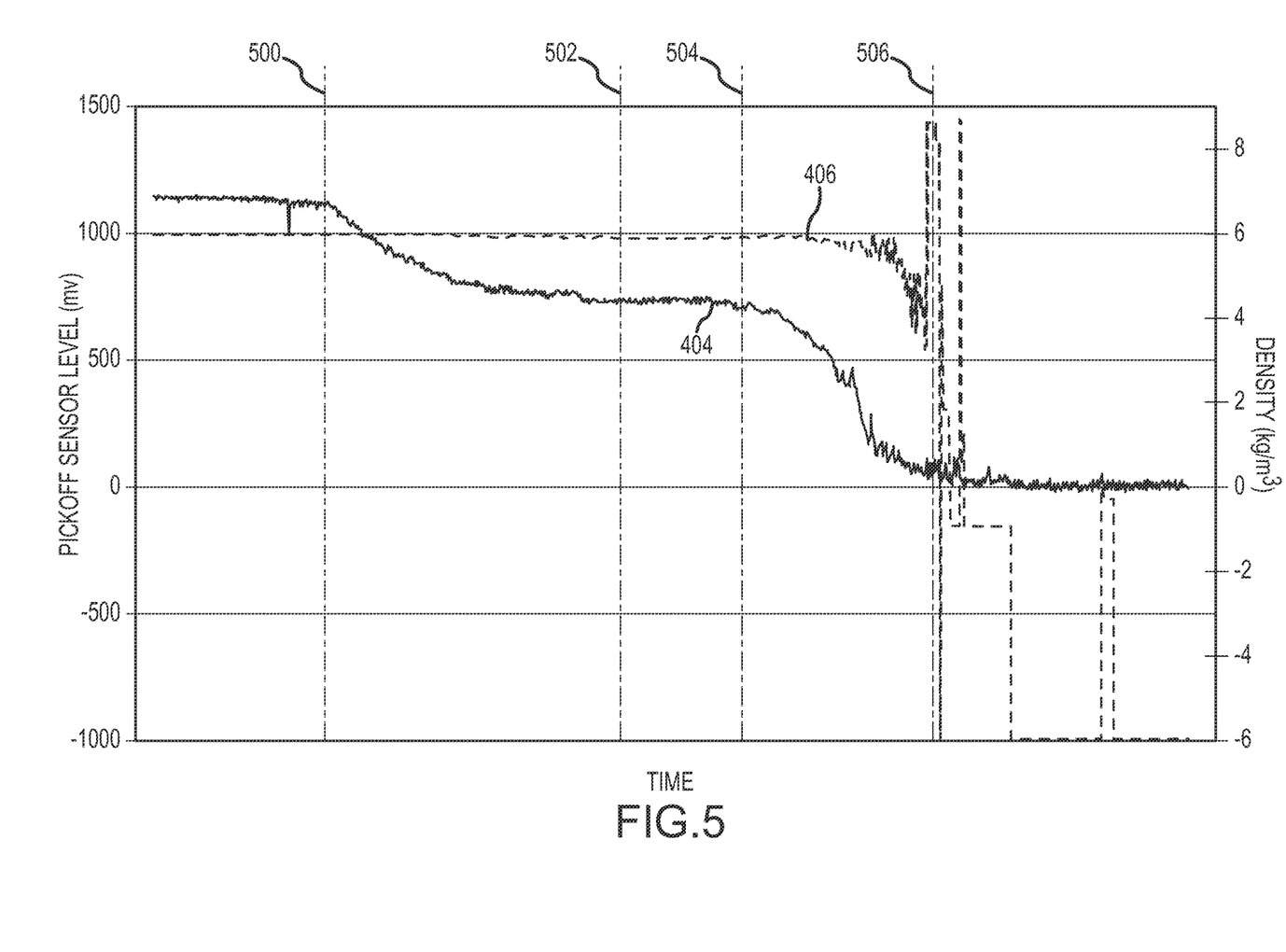
FIG. 5 is also a graph illustrating a sand separator with a liquid/solid interface detector in use.

FIG. 5 shows similar data for a vibratory meter 120 installed in a sand separator 100 wherein fine sand is introduced into the separator 100. Fine sand is introduced into the separator 100 at a first point 500. At a second time point 502, the addition of sand was paused. The vibratory element 122 at this point is interacting with a predominantly liquid phase of the liquid/solid mixture in the separator 100. The pickoff sensor output 404 reflects this by exhibiting a stable output voltage. The meter output 406 (measured as density in this example) concurrently remains stable as a function of the pickoff sensor output 404. At a third time point 504, the addition of sand is resumed, and the liquid/solid interface is initially detected by the meter 120. The vibratory element 122 at this point is interacting with an increasingly greater proportion of sand as liquid/solid interface rises. The pickoff sensor output 404 reflects this by exhibiting a decreasing output voltage. The meter output 406 concurrently decreases as a function of the pickoff sensor output 404. At a fourth time point 506, the vibratory element 122 is substantially buried by the sharp sand, and the vibratory element 122 is dampened to a point that the pickoff sensor output 404 is effectively about 0 mv. This, of course, is reflected by the meter output 406, which also declines and exhibits erratic readings.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other devices and method, and not just to the embodiments described above and shown in the accompanying figures. Accordingly, the scope of the invention should be determined from the following claims.

What is claimed is:

1. A sand separator (100) including a separation chamber (106) and a drain (118), comprising:

a meter (120) in fluid communication with an interior of the separation chamber (106), wherein the meter (120) is configured to detect a liquid/solid interface, wherein the meter comprises a vibratory element, a driver configured to vibrate the vibratory element, and a pickoff sensor configured to detect vibration of the vibratory element; and meter electronics (128) in electrical communication with the meter (120) configured to receive a signal from the meter (120), wherein the signal from the meter is a phase difference between a driver signal provided to the driver and a pickoff signal received from the pickoff sensor, and wherein meter electronics are configured to indicate when the vibratory meter is unable to maintain a fixed phase difference between the drive signal and the pickoff signal to detect the liquid/solid interface.

2. The sand separator (100) of claim 1, wherein the meter (120) is located proximate a level in the separation chamber (106) that corresponds to a maximum desired level of the liquid/solid interface.

3. The sand separator (100) of claim 2, wherein the vibratory meter is at least one of a densitometer and viscometer.

4. The sand separator (100) of claim 1, wherein the signal from the meter (120) is a signal strength of the pickoff sensor (126).

5. The sand separator (100) of claim 4, wherein the signal strength is a voltage.

6. The sand separator (100) of claim 1, wherein the drain (118) is remotely actuatable.

7. The sand separator (100) of claim 1, wherein the driver (124) comprises a piezoelectric element, and the pickoff sensor (126) comprises a piezoelectric element.

8. A sand separator (100) including a separation chamber (106) and a drain (118), comprising:
a vibratory fork densitometer (120) in fluid communication with an interior of the separation chamber (106) that is configured to indicate a liquid/solid interface;
a vibratory element (122) of the fork densitometer (120) that is configured to vibrate;
a driver (124) configured to receive a driver signal, wherein the driver (124) is further configured to vibrate the vibratory element (122);
a pickoff sensor (126) configured to detect a vibration of the vibratory element (122) and generate a pickoff signal that represents the vibration detected; and
meter electronics (128) in electrical communication with the densitometer (120) configured to provide the driver signal to the driver (124) and receive the pickoff signal from the densitometer (120), wherein the meter electronics calculates a phase difference between the driver signal and the pickoff signal and determines the presence of the liquid/solid interface when a fixed said phase difference can no longer be maintained.

9. The sand separator (100) of claim 8, wherein the pickoff signal is a signal strength of the pickoff sensor (126).

10. The sand separator (100) of claim 9, wherein the pickoff signal strength is a voltage.

11. The sand separator (100) of claim 8, further comprising a drain (118) configured to release material from the sand separator (100).

12. The sand separator (100) of claim 11, wherein the drain (118) comprises a valve that is actuatable by the meter electronics (128).

13. A method of detecting a liquid/solid interface in a sand separator comprising the steps of:
placing a vibratory meter in a sand separator;
vibrating a vibratory element of the vibratory meter at a resonant frequency of the vibratory element and fluid surrounding the vibratory element;
receiving a signal from a pickoff sensor of the vibratory meter;
detecting a presence of the liquid/solid interface by maintaining a fixed phase difference between a drive signal and a pickoff signal; and
indicating when the vibratory meter is unable to maintain the fixed phase difference between the drive signal and the pickoff signal.

14. The method of detecting a liquid/solid interface in a sand separator of claim 13, wherein the fixed phase difference is approximately 45°.

15. The method of detecting a liquid/solid interface in a sand separator of claim 13, wherein the step of detecting the presence of the liquid/solid interface further comprises the step of:
indicating when a phase difference between the drive signal and the pickoff signal fluctuates from the fixed phase difference by greater than a predetermined amount.

16. The method of detecting a liquid/solid interface in a sand separator of claim 13, wherein the step of detecting the presence of the liquid/solid interface further comprises the step of:
indicating when the vibratory element ceases to vibrate.

17. The method of detecting a liquid/solid interface in a sand separator of claim 13, wherein the step of detecting the presence of the liquid/solid interface further comprises the step of:
indicating the presence of the liquid/solid interface in the sand separator if an intensity of the vibrational response is below a predetermined threshold.

18. The method of detecting a liquid/solid interface in a sand separator of claim 17, wherein the step of detecting the presence of the liquid/solid interface wherein the intensity comprises a voltage.

19. The method of detecting a liquid/solid interface in a sand separator of claim 13, further comprising the step of:
emptying solids from the sand separator if the liquid/solid interface is detected.

20. The method of detecting a liquid/solid interface in a sand separator of claim 13, further comprising the step of:
opening a drain of the sand separator.

* * * * *